US009598815B2

(12) United States Patent
Okada et al.

(10) Patent No.: US 9,598,815 B2
(45) Date of Patent: *Mar. 21, 2017

(54) REDUCING AGENT, INK-JET RECORDING APPARATUS, DISCHARGE PRINTING METHOD, IMAGE FORMING METHOD, REDUCING AGENT STABILIZING METHOD, AND REDUCING AGENT ENHANCING METHOD

(71) Applicant: BROTHER KOGYO KABUSHIKI KAISHA, Nagoya (JP)

(72) Inventors: Goro Okada, Nagoya (JP); Kunihiro Fujita, Nagoya (JP)

(73) Assignee: Brother Kogyo Kabushiki Kaisha, Nagoya-shi (JP)

( * ) Notice: Subject to any disclaimer, the term of this patent is extended or adjusted under 35 U.S.C. 154(b) by 44 days.

This patent is subject to a terminal disclaimer.

(21) Appl. No.: 14/628,506

(22) Filed: Feb. 23, 2015

(65) Prior Publication Data
US 2015/0252520 A1 Sep. 10, 2015

(30) Foreign Application Priority Data

Mar. 10, 2014 (JP) .................................. 2014-046832
Dec. 22, 2014 (JP) .................................. 2014-259458

(51) Int. Cl.
| | |
|---|---|
| *D06L 3/10* | (2006.01) |
| *D06P 5/00* | (2006.01) |
| *C07C 323/52* | (2006.01) |
| *C07C 381/14* | (2006.01) |
| *B41J 2/01* | (2006.01) |

(Continued)

(52) U.S. Cl.
CPC . *D06L 3/10* (2013.01); *B41J 2/01* (2013.01); *B41J 3/4078* (2013.01); *B41J 11/0015* (2013.01); *C07C 323/52* (2013.01); *C07C 381/14* (2013.01); *D06P 5/001* (2013.01)

(58) Field of Classification Search
CPC ........................................................ D06L 3/10
See application file for complete search history.

(56) References Cited

U.S. PATENT DOCUMENTS

| | | |
|---|---|---|
| 2,248,128 A | 7/1941 | Seymour et al. |
| 4,197,256 A | 4/1980 | Sato et al. |
| 4,244,690 A | 1/1981 | Sato et al. |

(Continued)

FOREIGN PATENT DOCUMENTS

| | | |
|---|---|---|
| EP | 2537679 A1 | 12/2012 |
| JP | H08-35188 A | 2/1996 |

(Continued)

OTHER PUBLICATIONS

Extended European Search Report issued in the corresponding European Patent Application No. 15156229.5 dated Jul. 17, 2015.

*Primary Examiner* — An Do
*Assistant Examiner* — Renee I Wilson
(74) *Attorney, Agent, or Firm* — Fox Rothschild LLP

(57) ABSTRACT

The present invention relates to a reducing agent containing thiourea dioxide. The reducing agent contains thiourea. The reducing agent contains carboxylate. The carboxylate includes at least one of aliphatic monocarboxylate, an aliphatic monocarboxylic acid derivative salt, and malonate. Therefore, the reducing agent exerts a good reducing ability and a good long-term stability effect.

16 Claims, 4 Drawing Sheets

(51) Int. Cl.
*B41J 11/00* (2006.01)
*B41J 3/407* (2006.01)

(56) References Cited

U.S. PATENT DOCUMENTS

| | | | | |
|---|---|---|---|---|
| 4,943,661 A | * | 7/1990 | Nitoh | C07C 381/14 |
| | | | | 564/26 |
| 5,846,266 A | * | 12/1998 | Rattee | D06P 1/62 |
| | | | | 8/457 |
| 2008/0006176 A1 | * | 1/2008 | Houjou | C09D 11/322 |
| | | | | 106/31.13 |
| 2008/0250967 A1 | | 10/2008 | Souma et al. | |
| 2014/0289974 A1 | | 10/2014 | Okada et al. | |

FOREIGN PATENT DOCUMENTS

| | | |
|---|---|---|
| JP | 2008-255300 A | 10/2008 |
| JP | 2009-069265 A | 4/2009 |

* cited by examiner

REDUCING AGENT, INK-JET RECORDING APPARATUS, DISCHARGE PRINTING METHOD, IMAGE FORMING METHOD, REDUCING AGENT STABILIZING METHOD, AND REDUCING AGENT ENHANCING METHOD

CROSS-REFERENCE TO RELATED APPLICATION

This application claims priority from Japanese Patent Application Nos. 2014-46832 filed on Mar. 10, 2014 and 2014-259458 filed on Dec. 22, 2014. The entire subject matter of the Japanese Patent Application is incorporated herein by reference.

The present invention relates to a reducing agent, an ink-jet recording apparatus, a discharge printing method, an image forming method, a reducing agent stabilizing method, and a reducing agent enhancing method.

BACKGROUND

A reducing agent contains thiourea dioxide, for example. The thiourea dioxide having a reducing ability is used in a discharge printing agent, a bleaching agent, or a deinking agent, for example.

In the case where thiourea dioxide is used in a reducing agent, it is required to dissolve the thiourea dioxide in water. However, the solubility of the thiourea dioxide in water is a few wt % which is low. Since the reducing agent may only contain little amount of thiourea dioxide relative to the total amount of the reducing agent, there is a possibility that the reducing ability is low when the thiourea dioxide is used alone as a reducing agent.

Thiourea dioxide is hydrolyzed in an aqueous solution over time, and the concentration thereof is reduced. Accordingly, the reducing ability of thiourea dioxide is reduced over time. For example, when thiourea dioxide is used in a discharge printing agent, the discharge printing effect is maintained only for a short period of time such as about a few weeks. Thus, for example, there is a problem in that the discharge printing ability is reduced when the reducing agent containing thiourea dioxide is stored for a long period of time such as a few months.

SUMMARY

The reducing agent comprises: thiourea dioxide; and carboxylate, and the carboxylate comprises at least one of aliphatic monocarboxylate, an aliphatic monocarboxylic acid derivative salt, and malonate.

The ink-jet recording apparatus comprises a liquid ejection unit that ejects a liquid and further comprises a unit that applies the reducing agent.

The discharge printing method comprises: a reducing agent applying step of applying the reducing agent to fabric; and a heating step of heating a reducing agent-applied area.

The image forming method comprises: a discharge printing step of performing discharge printing of fabric; and an image printing step of printing an image on a discharge printing-performed area using an ink, and the discharge printing step is performed by the discharge printing method.

The reducing agent stabilizing method is a method for stabilizing a reducing agent that comprises thiourea dioxide, comprising: adding carboxylate, wherein the carboxylate is at least one of aliphatic monocarboxylate, aliphatic monocarboxylic acid derivative salt, and malonate.

The reducing agent enhancing method is a method for enhancing a reducing agent that comprises thiourea dioxide, comprising: adding carboxylate, wherein the carboxylate is at least one of aliphatic monocarboxylate, aliphatic monocarboxylic acid derivative salt, and malonate.

DETAILED DESCRIPTION

Figure 1A:
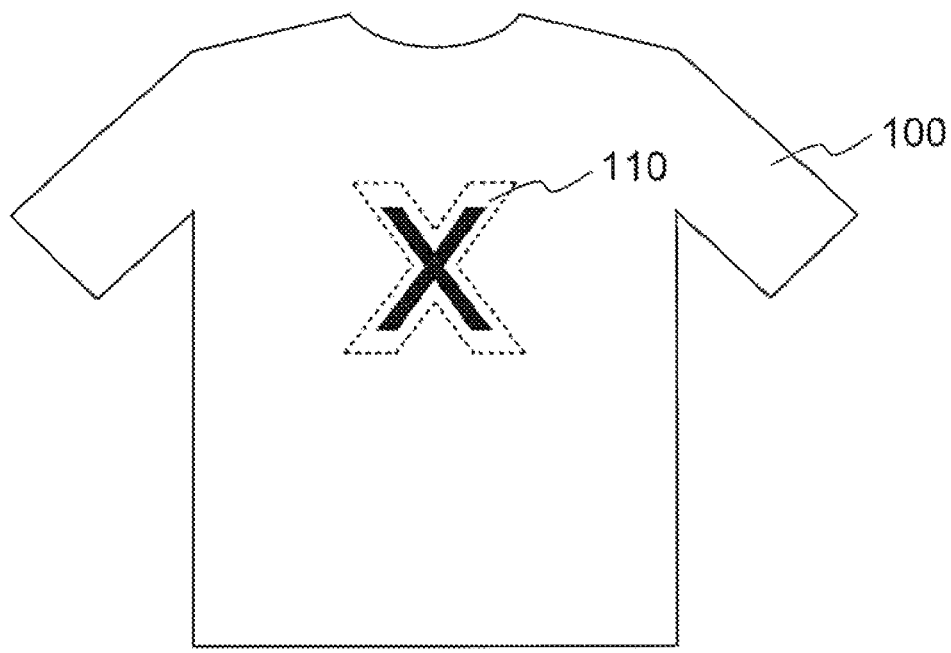
FIGS. 1A and 1B are figures showing an example of applying a reducing agent in the discharge printing method.

The embodiments of the present invention are described with reference to the drawings. The reducing agent is, for example, for use in discharge printing of fabric, a bleaching agent for waste paper, a pulp, and the like. The use of the reducing agent is not particularly limited.

Examples of fabric to be subjected to discharge printing include clothes such as a T-shirt, a bathing suit, and a sweat shirt; and cloth products such as a bag and shoes. The fabric encompasses a woven fabric and a knitted fabric. From the viewpoint of the discharge printing effect, a material of the fabric is, for example, a natural fiber. Examples of the natural fiber include cotton and silk. The material of the fabric may be a blended fabric obtained by mixing plural kinds of fibers. The discharge printing of the present embodiment is different in reaction process and object to be subjected to discharge printing from bleaching usually performed in the home and the like, for example. Specifically, in the bleaching performed in the home and the like, clothes are immersed in an agent and allowed to stand, and the agent chemically decomposes stains themselves by an oxidation reaction or a reduction reaction. In contrast, an agent for discharge printing directly acts on dye molecules which specifically dye cotton fibers of fabric and chemically decomposes the dye molecules. In the reaction process of discharge printing, for example, fabric is immersed in an agent, allowed to stand, and heated at 100° C. or more using a device such as a heat press. The discharge printing includes a reaction process in the presence of high-temperature steam. In the presence of high-temperature steam, for example, thiourea dioxide (aminoiminomethanesulfinic acid) which is a main component is decomposed. Accordingly, sulfoxylic acid having a reducing ability is generated. Thus, the chemical reaction in which sulfoxylic acid acts on the dye molecules is assumed.

Thiourea dioxide has a potent decolorization effect on a dye pigment. A reaction of thiourea dioxide with oxygen in the air is slow.

The reducing agent comprises thiourea dioxide and specific carboxylate described below. Since thiourea dioxide and the specific carboxylate are used in combination in the reducing agent, a good reducing effect and a good long-term stability effect are exerted. A process of exerting an effect of the reducing agent is considered as follows, for example.

The reducing effect is, for example, a decolorization effect, a bleaching effect, or the like of decomposing molecules of dyes, stains, and the like by a nucleophilic reaction of molecules of the reducing agent with the molecules of dye, stains, and the like. Carboxyl carbon and a carbon in carboxylate are in a position of being easily subjected to a nucleophilic attack. A portion easily subjected to a nucleophilic attack in the frontier orbital theory is a portion with a high electron density in an orbit with the lowest energy level (LUMO (Lowest Unoccupied Molecular Orbital)) among molecular orbits that are not occupied with electrons. The inventors of the present invention calculated the electron density of the specific carboxylate on the basis of the extended Huckel method using calculation software such as Chem3D (manufactured by Cambridge Soft). The calculated value was in a value range in which a good reducing effect is exerted. Therefore, a reaction of thiourea dioxide with oxygen that was present in an aqueous solution or air was inhibited. It may be assumed that the specific carboxylate attributes to long-term stability of thiourea dioxide. Carboxylate having a molecular structure which has no steric inhibition factor such as formate is effective in catalysis at the time of heating, for example. It is assumed that the structure having no steric inhibition factor causes a nucleophilic reaction with molecules of dyes and the like to be easily occurred, and accordingly, the reducing effect is improved. The above-described reaction process is a mere assumption, and the present invention is not limited thereby.

The amount of the thiourea dioxide to be added relative to the total amount of the reducing agent is not particularly limited and is, for example, 0.5 wt % to 12.5 wt %, 0.5 wt % to 10 wt %, 0.5 wt % to 7.5 wt %, 1 wt % to 7.5 wt %, 2 wt % to 7.5 wt %, 3 wt % to 7.5 wt %, 4 wt % to 7.5 wt %, 5 wt % to 7.5 wt %. In the case where the reducing agent is used as a discharge printing agent for fabric, the amount of the thiourea dioxide to be added is not particularly limited and is, for example, in the range of 5 wt % to 7.5 wt %. Gas is generated in some cases at the time when the reducing agent is stored, and this generation of gas does not directly influence on the reducing ability. When the amount of the thiourea dioxide to be added is in the above-described range, gas is not generated at the time when the reducing agent is stored, and there is no possibility that a container containing the reducing agent is expanded or burst. For example, at the time when the reducing agent is ejected from a head of an ink-jet recording apparatus, a nozzle of the head is not closed by gas unless gas is generated from the reducing agent, and accordingly, the head may stably eject the reducing agent. Moreover, the reducing agent has a good discharge printing ability, so that it may be favorably used as a discharge printing agent for fabric.

The specific carboxylate is either one of or a combination of two or more of aliphatic monocarboxylate, an aliphatic monocarboxylic acid derivative salt, and malonate. Hereinafter, either one of or a combination of two or more of aliphatic monocarboxylate, an aliphatic monocarboxylic acid derivative salt, and malonate is referred to as specific carboxylate. The salt in the present invention is not particularly limited, and examples thereof include a metal salt and an ammonium metal salt. Examples of the metal salt include a sodium salt and a potassium salt.

Examples of the aliphatic monocarboxylate include: straight-chain aliphatic monocarboxylate such as formate, acetate, propionate, butyrate, valerate, caproic acid, enanthic acid, caprylic acid, pelargonic acid, capric acid, lauric acid, myristic acid, pentadecylic acid, palmitic acid, margaric acid, stearic acid, oleic acid, vaccenic acid, linoleic acid, arachidic acid, or arachidonic acid; and branched aliphatic monocarboxylate such as isobutyric acid, isovaleric acid, pivalate, triethyl acetic acid, or 2,2-dimethyl butanoic acid. The aliphatic monocarboxylate is, for example, formate, laurate, or pivalate.

Examples of the aliphatic monocarboxylic acid derivative salt include: hydroxyl group-containing monocarboxylate such as glycolate, lactate, glycerate, or hydroxybutyrate; a thiol group-containing carboxylate such as thioglycolate; and halogen-containing carboxylate such as monochloroacetate, dichloroacetate, trichloroacetate, α-chlorobutyrate, β-chlorobutyrate, γ-chlorobutyrate, monofluoroacetate, difluoroacetate, or trifluoroacetate. The aliphatic monocarboxylic acid derivative salt is, for example, trifluoroacetate.

The malonate is monomalonate or dimalonate and is, for example, dimalonate.

One kind of the specific carboxylate may be used alone, or two or more kinds of the specific carboxylate may be used in combination. The amount of the specific carboxylate to be added relative to the total amount of the reducing agent is not particularly limited and is, for example, 0.5 wt % to 10 wt %, 1 wt % to 10 wt %, 2.5 wt % to 10 wt %, 2.5 wt % to 7.5 wt %, 5 wt % to 7.5 wt %. When the amount of the specific carboxylate to be added is in the above-described range, a reducing agent having a good discharge printing ability may be obtained.

A combination of the amount of the thiourea dioxide to be added and the amount of the specific carboxylate to be added is not particularly limited, and is, for example, a combination of 4 wt % to 10 wt % and 2.5 wt % to 7.5 wt %, a combination of 5 wt % to 10 wt % and 2.5 wt % to 7.5 wt %, a combination of 5 wt % to 7.5 wt % and 2.5 wt % to 7.5 wt %. Gas is generated in some cases at the time when the reducing agent is stored, and this gas does not directly influence on the reducing ability. However, when the amount of the thiourea dioxide to be added and the amount of the specific carboxylate to be added are in the above-described range, a reducing agent having a good discharge printing ability may be obtained without generating gas.

The reducing agent may further comprise a pH adjusting agent. The pH adjusting agent is not particularly limited and is a base such as amine. The amine is not particularly limited, and examples thereof include ammonia, primary amine, secondary amine, and tertiary amine. The amine is, for example, primary amine. The amine may have one or more amino groups. Examples of the primary amine include aminoalcohol, a guanidine salt, a guanidine derivative, and N,N'-bis(2-aminoethyl)-1,2-ethanediamine. Examples of the aminoalcohol include 2-amino-2-hydroxymethyl-1,3-propanediol (AHP), 2-amino-2-methyl-1-propanol (AMP), 2-amino-2-ethyl-1,3-propanediol (AEP), and 2-(2-aminoethoxy)ethanol (AEE). The guanidine salt is, for example, guanidine carbonate. The guanidine derivative is, for example, aminoguanidine sulfate. The primary amine is, for example, 2-amino-2-hydroxymethyl-1,3-propanediol (AHP), 2-amino-2-methyl-1-propanol (AMP), or 2-amino-2-ethyl-1,3-propanediol (AEP). The primary amine is, for example, 2-amino-2-methyl-1-propanol (AMP).

One kind of the pH adjusting agent may be used alone, or two or more kinds of the pH adjusting agent may be used in combination. The pH of the reducing agent is maintained to alkaline by the pH adjusting agent. Accordingly, the deterioration of the thiourea dioxide caused by hydrolysis of the thiourea dioxide at the time when the reducing agent is stored for a long period of time may be suppressed. The pH is, for example, 8 to 10, 8 to 9.

The reducing agent may further comprise at least one of urea and ketone. The ketone encompasses all of carbonyl compounds such as aldehyde, carboxylic acid, and ester and salts, ions, and hydrates thereof. The ketone is, for example, β-diketone or an acetone derivative.

Examples of the β-diketone include acetylacetone, malonic acid, 3-acetyl-γ-butyrolactone, dehydroacetic acid, and methyl acetoacetate. The β-diketone is, for example, acetylacetone, 3-acetyl-γ-butyrolactone, dehydroacetic acid, methyl acetoacetate, or N-methyl acetoacetic acid amide.

The acetone derivative is, for example, a compound represented by the following general formula (1):

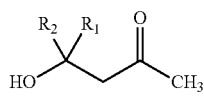

In the general formula (1), $R_1$ and $R_2$ each represents an alkyl group or hydrogen and may be identical to or different from each other. The alkyl group is not particularly limited and is, for example, an alkyl group with a carbon number of 1 to 20. The alkyl group may be, for example, a straight-chain alkyl group or a branched alkyl group. Examples of the alkyl group include a methyl group, an ethyl group, a n-propyl group, an isopropyl group, a n-butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group. The compound represented by the general formula (1) is, for example, 2-hydroxy-2-methyl-4-pentanon. The acetone derivative is, for example, 2-hydroxy-2-methyl-4-pentanon.

One kind of the ketone may be used alone, or two or more kinds of the ketone may be used in combination. The ketone is used together with urea in combination, for example. The amount of the ketone to be added relative to the total amount of the reducing agent is not particularly limited and is, for example, 5 wt % to 15 wt %.

The reducing agent may further comprise water. The water is, for example, ion-exchange water or pure water. The amount of the water to be added relative to the total amount of the reducing agent is, for example, the balance of the other components.

The reducing agent may further comprise a water-soluble organic solvent. As the water-soluble organic solvent, any of conventionally known organic solvents may be used. Examples of the water-soluble organic solvent include poly-alcohol, a polyalcohol derivative, alcohol, amide, ketone, ketoalcohol, ether, a nitrogen-containing solvent, a sulfur-containing solvent, propylene carbonate, ethylene carbonate, and 1,3-dimethyl-2-imidazolidinone. Examples of the polyalcohol include glycerin (Gly), ethylene glycol, diethylene glycol (DEG), propylene glycol, butylene glycol, hexylene glycol, triethylene glycol, polyethylene glycol, dipropylene glycol, tripropylene glycol, polypropylene glycol, trimethylolpropane, 1,5-pentanediol, and 1,2,6-hexanetriol. Examples of the polyalcohol derivative include ethylene glycol methyl ether, ethylene glycol ethyl ether, ethylene glycol-n-propyl ether, ethylene glycol-n-butyl ether, diethylene glycol methyl ether, diethylene glycol ethyl ether, diethylene glycol-n-propyl ether, diethylene glycol-n-butyl ether, diethylene glycol-n-hexyl ether, triethylene glycol methyl ether, triethylene glycol ethyl ether, triethylene glycol-n-propyl ether, triethylene glycol-n-butyl ether, propylene glycol methyl ether, propylene glycol ethyl ether, propylene glycol-n-propyl ether, propylene glycol-n-butyl ether, dipropylene glycol methyl ether, dipropylene glycol ethyl ether, dipropylene glycol-n-propyl ether, dipropylene glycol-n-butyl ether, tripropylene glycol methyl ether, tripropylene glycol ethyl ether, tripropylene glycol-n-propyl ether, and tripropylene glycol-n-butyl ether. Examples of the alcohol include methyl alcohol, ethyl alcohol, n-propyl alcohol, isopropyl alcohol, n-butyl alcohol, sec-butyl alcohol, isobutyl alcohol, tert-butyl alcohol, and benzyl alcohol. Examples of the amide include dimethylformamide and dimethylacetamide. The ketone is, for example, acetone. The ketoalcohol is, for example, diacetone alcohol. Examples of the ether include tetrahydrofuran and dioxane. Examples of the nitrogen-containing solvent include pyrolidone, 2-pyrolidone, N-methyl-2-pyrolidone, cyclohexylpyrolidone, and triethanolamine. Examples of the nitrogen-containing solvent include thiodiethanol, thiodiglycol, thiodiglycerol, sulfolane, and dimethyl sulfoxide. The amount of the water-soluble organic solvent to be added relative to the total amount of the reducing agent is, for example, 0.5 wt % to 30 wt %, for example, 5 wt % to 30 wt %, for example, 10 wt % to 20 wt %. One kind of the water-soluble organic solvent may be used alone, or two or more kinds of the water-soluble organic solvent may be used in a combination.

The water-soluble organic solvent is, for example, glycerin or diethylene glycol each of which is a high boiling point solvent and is, for example, glycerin. The amount of the high boiling point solvent to be added relative to the total amount of the reducing agent is, for example, 0.5 wt % to 30 wt %, for example, 5 wt % to 30 wt %, for example, 10 wt % to 20 wt %.

The reducing agent may further comprise a conventionally known additive. Examples of the additive include a surfactant, a viscosity modifier, a surface tension regulator, an antioxidant, and an anti-mold agent. Examples of the viscosity modifier include polyvinyl alcohol, cellulose, and a water-soluble resin. The reducing agent may be prepared by mixing components other than the thiourea dioxide and the specific carboxylate in advance and thereafter adding the thiourea dioxide and the specific carboxylate.

Figure 3:
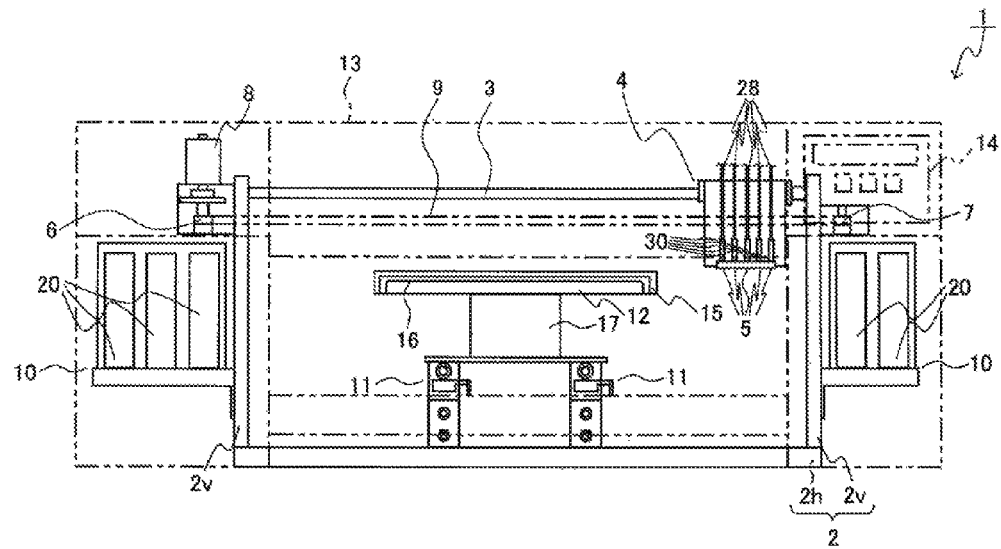
FIG. 3 is a front view showing an example of a configuration of an ink-jet recording apparatus.

The container containing the reducing agent is described. The container contains the reducing agent of the present invention. As shown in FIG. 3, the container is, for example, a conventionally known container that is the same as an ink tank 20 of an ink-jet recording apparatus 1. For example, the container is an ink cartridge having a case made of a resin. For example, the container is an ink pack formed of a flexible film. When the reducing agent is introduced into a flexible ink pack, an impact is generated, and accordingly, there is a possibility that a chemical reaction is progressed by the impact. If a reduction in discharge printing ability is a concern, the reducing agent may be stored in a container having a case. The reducing agent may be stored in a flexible ink pack arranged in a case. Only a solid of the reducing agent may be introduced into the container and may thereafter be mixed with a liquid.

The ink-jet recording apparatus comprises: a liquid ejection mechanism that ejects a liquid; and a mechanism that applies a reducing agent. Examples of the liquid include an ink for ink-jet recording and a treatment liquid for use in ink-jet recording. For example, the ink-jet recording apparatus includes a storage section of storing the container, and a liquid in the container stored in the storage section is ejected by the liquid ejection mechanism. As shown in FIG.

2, the ink-jet recording apparatus 1 comprises a mechanism that applies a reducing agent, for example. Examples of the mechanism that applies a reducing agent include an ink-jet head, a spray, a stamp that applies a reducing agent to fabric, a brush, and a roller. The ink-jet recording apparatus of the present embodiment includes an ink-jet head 5 as the mechanism that applies a reducing agent.

The discharge printing method that is an example of a reducing method is described. The discharge printing method is a method for discharge printing of fabric, comprising: a reducing agent applying step of applying a reducing agent to fabric; and a heating step of heating a reducing agent-applied area.

In the reducing agent applying step, a reducing agent is applied by a method such as an ink-jet method of applying a reducing agent using an ink-jet head, a spray method, a stamp application, a brush application, or a roller application, for example.

Figure 1B:
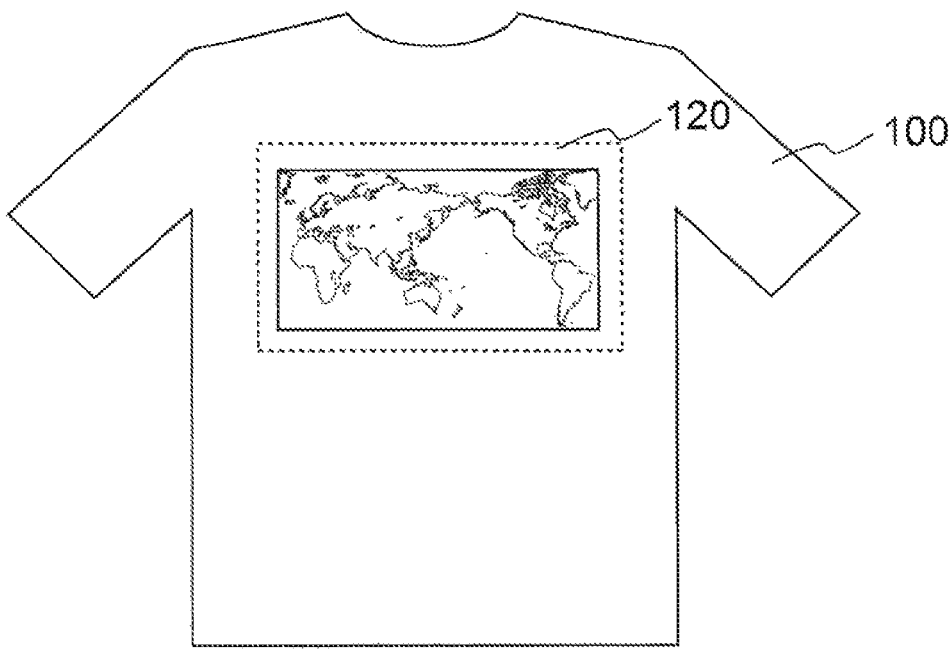

In the reducing agent applying step, a reducing agent may be applied to the entire surface or a part of the surface of fabric on which an image is formed. When a reducing agent is applied to a part of the surface on which an image is formed, a region mostly the same as an area in which printing is performed with an ink on the surface of fabric on which an image is formed is a reducing agent-applied area, for example. When a reducing agent is applied to a part of the surface on which an image is formed, the size of the reducing agent-applied area may be bigger than the area in which printing with an ink is performed. As shown in FIG. 1A, for example, when a character (X) is printed on fabric 100 such as a T-shirt, a reducing agent-applied area 110 with a line width higher than the line width of the character is formed. As shown in FIG. 1B, for example, when a pattern is printed on fabric 100, a reducing agent-applied area 120 having an area bigger than the pattern is formed.

The heating step is a step of heating a reducing agent-applied area. The heating step may be performed using an iron, a hot press device, an oven, or a conveyor belt oven, for example. When the iron or the hot press device is used, for example, the reducing agent-applied area is heated in the state where a Teflon (registered trademark) sheet having a flat surface is placed on the area, for example. Thus, generation of a nap of the fabric may be suppressed. For example, when the discharge printing method is used in the image forming method described below, an image may be printed more smoothly on fabric. The heating temperature is not particularly limited and is, for example, 160° C. to 185° C.

The image forming method is described. The image forming method is a method for forming an image on fabric, comprising: a discharge printing step of performing discharge printing of fabric; and an image printing step of printing an image on a discharge printing-performed area using an ink.

The image forming method may comprise a step such as a heat-fixing step described below in addition to the discharge printing step and the image printing step, for example.

The discharge printing step is the same as described in the discharge printing method of the present invention.

The image printing step is a step of printing an image on a discharge printing-subjected area or a reducing agent-applied area using an ink. When an image is printed on a reducing agent-applied area or a reducing agent non-applied area with an ink after discharge printing, the heating step may be performed after printing an image with an ink. The ink for use in the image printing step is not particularly limited, and is, for example, a pigment ink, a dye ink, or the like and is, for example, a pigment ink.

Figure 2:
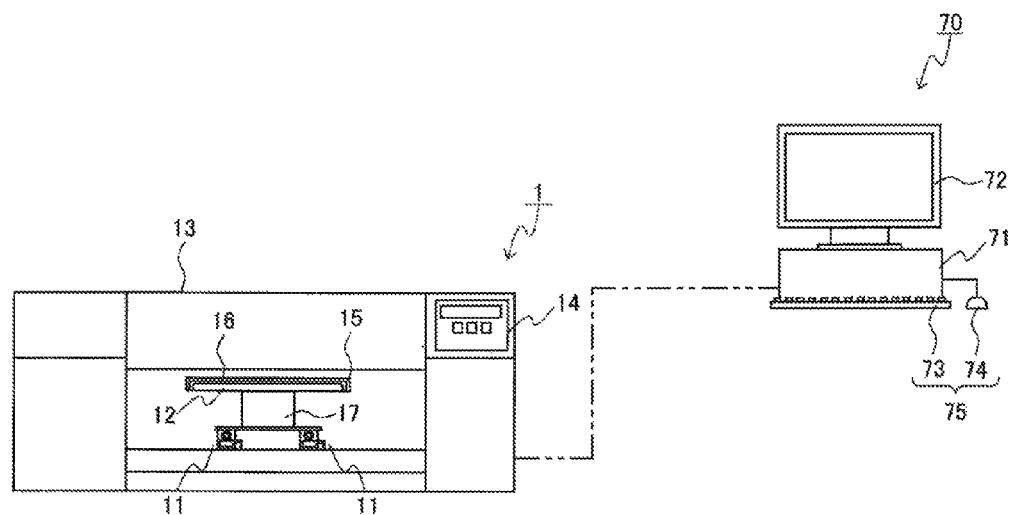
FIG. 2 is a schematic view showing an example of a configuration of an ink-jet recording apparatus.

As shown in FIG. 2, the image printing step is performed in the ink-jet recording apparatus 1, for example. The ink-jet recording apparatus 1 of the present embodiment performs the image printing step by an ink-jet method. The ink-jet recording apparatus 1 prints an image by ejecting an ink on fabric. A printing control device 70 acquires an image data of an image to be printed and controls the ink-jet recording apparatus 1. The ink-jet recording apparatus 1 connects the printing control device 70 via an interface.

As shown in FIG. 3, the ink-jet recording apparatus 1 includes a frame 2 that is a frame body. The frame 2 includes a horizontal part 2h located on the bottom part of the ink-jet recording apparatus 1 and two vertical parts 2v which are perpendicular to the both ends of the horizontal part 2h. In FIG. 3, identical parts to those in FIG. 2 are denoted by identical reference numerals. The same applies to drawings subsequent to FIG. 4. A slide rail 3 links upper parts of the two vertical parts 2v with each other. The slide rail 3 includes a carriage 4 so as to be slidable along the longitudinal direction in FIG. 3 of the slide rail 3. The lower surface of this carriage 4 is provided with five piezoelectric ink-jet heads 5 according to the respective colors in order to eject five color inks. The ink-jet recording apparatus 1 may be provided with eight ink-jet heads, for example. For example, two head units in each of which four ink-jet heads are disposed along a direction of moving the cartridge (hereinafter also referred to as "cartridge moving direction") may be arranged along the direction orthogonal to the cartridge moving direction. In this instance, one head unit includes four ink-jet heads of ejecting the respective four color inks of cyan, magenta, yellow, and black, and the other head unit includes two ink-jet heads of ejecting a white ink and two ink-jet heads of ejecting the reducing agent.

The respective upper parts of the two vertical parts 2v are supported by pulleys 6 and 7, and the pulley 6 is linked with a motor axis of a motor 8 supported by the vertical part 2v. An endless belt 9 bridges the pulleys 6 and 7. The carriage 4 is fixed in the endless belt 9.

When the pulley 6 is rotated in the forward direction and the reverse direction by driving the motor 8, the carriage 4 is driven to reciprocate along the slide rail 3. Thus, the ink-jet heads 5 are reciprocated.

Each of the two vertical parts 2v includes a mounting part 10 which detachably mounts ink tanks 20. One of the two mounting parts 10 mounts two color ink tanks 20, and the other mounting part 10 mounts three color ink tanks 20. Ink bags (not shown) in the respective ink tanks 20 are connected to the respective five sub tanks 30 at the upper parts of the ink-jet heads 5 via flexible tubes 28. The five sub tanks 30 are communicated with the respective ink-jet heads 5, so that each ink is supplied from each ink tank 20 to each ink-jet head 5.

Slide mechanisms 11 are provided above the horizontal part 2h of the frame 2. A platen 12 is supported above the slide mechanisms 11. The platen 12 includes a fixing frame 15. Fabric is arranged between the platen 12 and the fixing frame 15 so as to face a part to be subjected to printing up. The number of the platens 12 is one. However, the number of the platens 12 is not limited to one and may be increased as required. For example, in the case where an ink-jet recording apparatus has two platens, while an operator performs printing of an image on a T-shirt fixed on one of the platens, a T-shirt may be fixed on the other platen. Thus, operating efficiency is improved.

The ink-jet recording apparatus 1 includes a platen convey mechanism in order to reciprocate the platen 12 in a direction perpendicular to FIG. 3. The platen convey mechanism is, for example, a mechanism using a rack, a pinion mechanism, or an endless belt, for example.

Figure 4A:
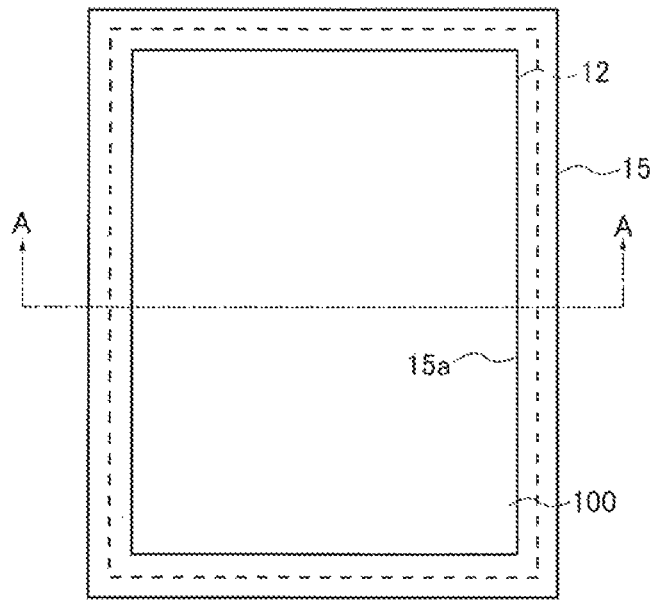
FIG. 4A is a plan view showing the state where fabric is set to a platen of an ink-jet recording apparatus.
Figure 4B:
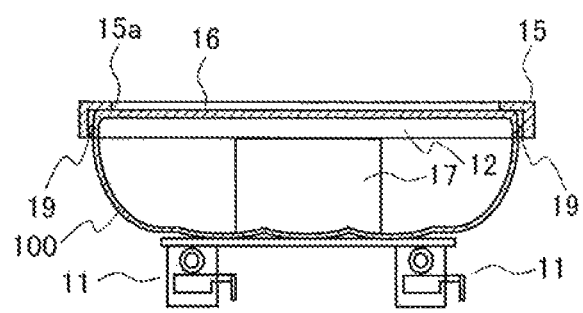
FIG. 4B is a cross-sectional view taken along line A-A of FIG. 4A.

As shown in FIG. 4A, the platen 12 has a rectangular shape whose longitudinal direction is a direction orthogonal to the direction of reciprocating the carriage 4 in plan view. As shown in FIG. 4B, the platen 12 has a supporting surface 16 of supporting the T shirt 100 as an example of an object to be subjected to printing. The lower surface of the platen 12 is linked with the upper end of the supporting member 17, and the lower end of the supporting member 17 is linked with the slide mechanism 11.

The fixing frame 15 covers four sides of the supporting surface 16 of the platen 12. The fixing frame 15 includes an opening 15a having an opening area slightly smaller than the area of the supporting surface 16 of the platen 12. The inner surface of the fixing frame 15, facing a side surface of the platen 12, includes an anti-slipping member 19 made of rubber. The fixing frame 15 has the anti-slipping member 19, so that when an operator sets the T-shirt 100 on the platen 12, the T-shirt 100 may be set in the state where it is pulled in both of the longitudinal direction and the short direction of the supporting surface 16 of the platen 12. The platen 12 holds the T-shirt 100 without creases. When an operator sets the T-shirt 100 on the platen 12, the T-shirt 100 is overlaid on the supporting surface 16 of the platen 12 from the hem side of the T-shirt 100 and is fixed with the fixing frame 15. A rotating part (not shown) which is capable of rotating the fixing frame 15 is provided at the end part of the platen 12 on the back side. An operator overlays the T-shirt 100 on the platen 12, and the fixing frame 15 is thereafter rotated to fit in the platen 12. Thus, the T-shirt 100 is sandwiched between the platen 12 and the fixing frame 15 and is fixed.

The ink-jet recording apparatus 1 includes a cover 13. The cover 13 protects the ink-jet heads 5, the slide mechanisms 11, and the like by covering them. In FIG. 3, in order to show the inside of the cover 13, the cover 13 is shown by a chain double-dashed line. An operation panel 14 including a liquid crystal panel and an operation button is provided in an upper right part of the front surface of the cover 13.

The five ink-jet heads 5 corresponding to the respective five color inks of white, yellow, magenta, cyan, and black are arranged along the longitudinal direction of reciprocating the carriage 4. The five ink-jet heads 5 are linked with the respective ink tanks 20 via the respective flexible tubes 28 and the respective sub tanks 30. A configuration of supplying the inks to the respective ink-jet heads is, for example, a configuration disclosed in JP 2004-291461 A.

By linking the ink tanks 20 with the respective sub tanks 30 via the respective flexible tubes 28, the inks in the respective ink tanks 20 are introduced into the respective sub tanks 30. For example, the ink tanks 20 are capable of being provided at the positions at which the ink tanks 20 are easily replaced. Thus, when the inks in the respective ink tanks 20 are run out, the ink tanks 20 are easily replaced.

A small space is formed between the lower surfaces of the ink-jet heads 5 and the supporting surface 16 of the platen 12. When an image is printed on the T-shirt 100, a platen 12 conveys a part to be subjected to printing of the T-shirt 100 to the space. The carriage 4 causes the ink-jet heads 5 to reciprocate, and the ink-jet heads 5 eject inks on the T-shirt 100 from many ejection nozzles each having a small diameter, arranged in the bottom surfaces of the ink-jet heads 5. The ink-jet recording apparatus 1 prints a color image on the T-shirt 100.

As shown in FIG. 2, the printing control device 70 is, for example, a general purpose personal computer (PC). The printing control device 70 includes a main body 71, a display as a display section 72, and an operation section 75.

Figure 5:
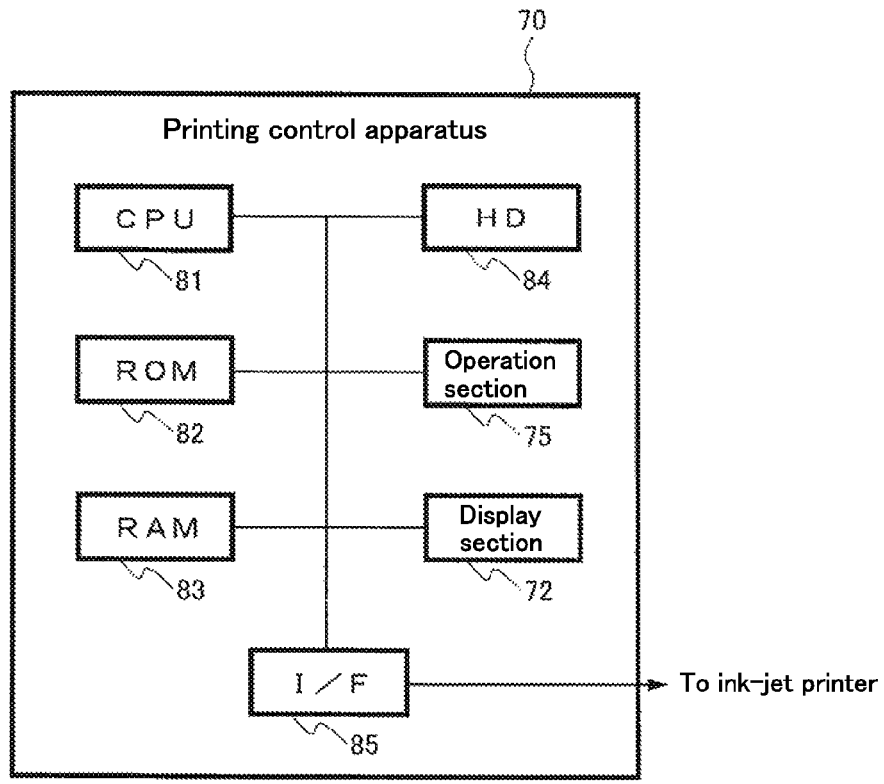
FIG. 5 is a block diagram showing a configuration of an ink-jet recording apparatus.

As shown in FIG. 5, the printing control device 70 includes a CPU (Central Processing Unit) 81, a ROM (Read Only Memory) 82, a RAM (Random Access Memory) 83, a HD (Hard Disk) 84, an operation section 75, a display section 72, and an interface (I/F) 85, and they are connected via a bus. The CPU 81, the ROM 82, the RAM 83, and the HD 84 are provided in the main body 71 of the printing control device 70. The operation section 75 includes a keyboard 73 and a mouse 74.

In order to control the operation of the printing control device 70, the HD 84 stores various programs. The HD 84 stores various image data produced by software and various data according to the kind of fabric such as a T-shirt. The CPU 81 performs various arithmetic processes on the basis of signals input with the operation section 75 and various programs and data stored in the ROM 82, the RAM 83, and the HD 84. The CPU 81 sends data and the like to the ink-jet recording apparatus 1 via the interface 85. The RAM 83 is a volatile storage device which is readable and writable and stores results of the various operations and the like in the CPU 81. The interface 85 is connected to an interface of the ink-jet recording apparatus 1, so that the printing control device 70 and the ink-jet recording apparatus are capable of communicating with each other.

Figure 6:
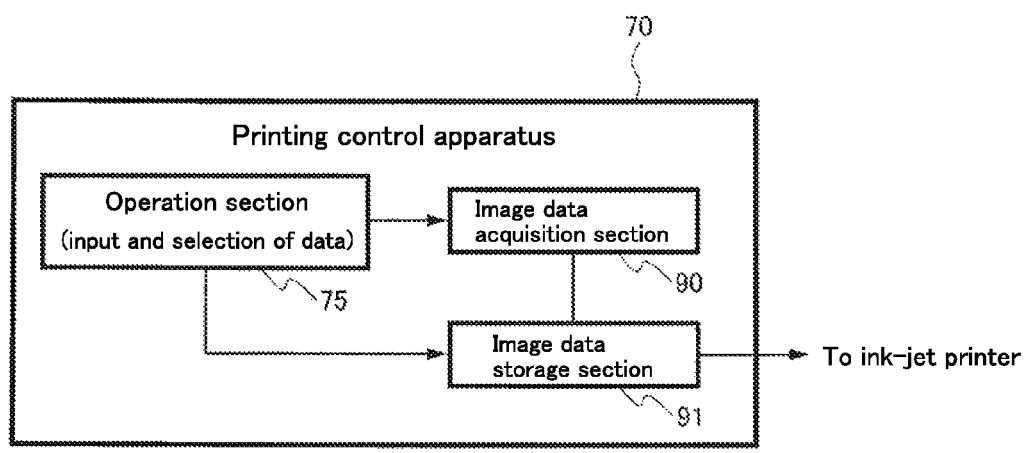
FIG. 6 is a block diagram of an ink-jet recording apparatus.

As shown in FIG. 6, the printing control device 70 includes an image data acquisition section 90 and an image data storage section 91. In the present embodiment, the CPU 81 is the image data acquisition section 90. The Ram 83 and the HD 84 are the image data storage section 91.

In order to produce image data, the image data acquisition section 90 has a known function. The image data acquisition section 90 produces image data on the basis of signals input from the keyboard 73 or the mouse 74 operated by an operator. The image data storage section 91 stores image data collected from removable storage media such as a CD-ROM, an FD, and an MO, the Internet, and the like and image data acquired in the image data acquisition section 90.

When an image is printed on the T-shirt 100 using the ink-jet recording apparatus 1, an operator firstly operates a keyboard 73 and a mouse 74 of a PC. The image data acquisition section 90 acquires image data to be printed on the T-shirt 100 on the basis of signals input through the keyboard 73 and the mouse 74. The image data is produced using software installed in the PC. The image data stored in the HD 84 in advance may be selected.

An operator fixes the T-shirt 100 on the platen 12. Specifically, an operator overlays the T-shirt 100 on the platen 12 from the hem of the T-shirt 100 and is fixed with a fixing frame 15 along a supporting surface of the platen 12 without creases.

An operator gives an instruction of performing printing via the operation section 75. The CPU 81 sends image data to the ink-jet recording apparatus 1 via the interface 85. The ink-jet heads 5 eject inks on the basis of the image data. The ink-jet recording apparatus 1 performs printing on the T-shirt 100 fixed on the platen 12.

The ink-jet recording apparatus 1 may include a heating mechanism. The heating mechanism may be any mechanism that is capable of performing a heat-fixing step described below in the ink-jet recording apparatus 1. The heating mechanism is, for example, a mechanism that may heat and pressurize a printing-subjected area of the fabric, such as a hot press mechanism or the like. The ink-jet recording apparatus 1 may include a pressurizing mechanism in addition to the heating mechanism. Any of the heating mechanism and the pressurizing mechanism may be performed in advance, or both of them may be performed simultaneously. The heat-fixing step may be performed by a device having a heating mechanism and a pressuring mechanism, different from the ink-jet recording apparatus 1.

The ink-jet recording apparatus 1 may not include an ink tank and an ink-jet head for a white ink. In the image forming method, an image is printed on fabric after being subjected to discharge printing. Thus, a color image may be formed on deep-color fabric without forming a base layer with a white ink.

In the present embodiment, the image printing step is performed by the ink-jet method. The present invention, however, is not limited thereto. The image printing step may be performed by screen printing, gravure printing, stencil, or the like using a conventionally known device or mechanism.

The image forming method may comprise a heat-fixing step of heat-fixing the inks on the fabric by subjecting the printing-subjected area of the fabric to a heat treatment after the image printing step. The heat-fixing step may be performed with the same device under the same conditions as in the heating step of the discharge printing method. The heat-fixing step may be performed using a device disclosed in JP 2009-209493 A. According to this device, the fabric may be heated at 180° C. and pressurized.

The reducing agent stabilizing method for stabilizing a reducing agent that comprises thiourea dioxide is described. The reducing agent stabilizing method comprises adding carboxylate. As the carboxylate, at least one of aliphatic monocarboxylate, aliphatic monocarboxylic acid derivative salt, and malonate is added. In the reducing agent stabilizing method, the conditions such as the amount of the carboxylate to be added and the like are the same as those in the above-mentioned reducing agent of the present invention.

The reducing agent enhancing method for enhancing a reducing agent that comprises thiourea dioxide is described. The reducing agent enhancing method comprises adding carboxylate, and as the carboxylate, at least one of aliphatic monocarboxylate, aliphatic monocarboxylic acid derivative salt, and malonate is added. In the reducing agent enhancing method, the conditions such as the amount of the carboxylate to be added and the like are the same as those in the above-mentioned reducing agent.

EXAMPLES

The examples are described together with a comparative example. The present invention, however, is not limited thereby.

Examples 1-1 to 1-8 and Comparative Example 1-9

Water, thiourea dioxide, specific carboxylate, and 2-amino-2-methyl-1-propanol (AMP) that is a pH adjusting agent in each reducing agent composition summarized in Table 1 were mixed, and ketone (N-methyl acetoacetic acid amide (NMAA)) was further added thereto. Thus, the reducing agents of Examples 1-1 to 1-8 were obtained. Three kinds of each of reducing agents of the examples and the comparative example with the three gradual amounts of thiourea dioxide to be added of 5 wt %, 3.75 wt %, and 2.5 wt % relative to the total amounts of the respective reducing agents were prepared. The same amounts of the specific carboxylate to be added, the pH adjusting agent to be added, and the ketone to be added relative to each of the total amounts of the respective three kinds of each of the reducing agents were used.

The reducing agent of Comparative Example 1-9 was obtained in the same manner as in Example 1-1 except that specific carboxylate was not added.

The enhancing effect and the storage stability effect of each of the reducing agents of the examples and the comparative example were evaluated by the following method. Each of the reducing agents of the examples and the comparative example immediately after the preparation was sprayed seven times, by a spray method, on each T-shirt (manufactured by Hanes, trade name: BEEFY (black)) on which a sheet obtained by cutting out 5 cm×5 cm had been placed. Then, a reducing agent-applied area was heated while moving an iron on the reducing agent-applied area in the state of placing a Teflon (registered trademark) sheet having a flat surface on the reducing agent-applied area. Subsequently, the T-shirt was washed with a washing machine using a detergent and was thereafter natural-dried in the shade. The degree of discharge printing of the T-shirt was evaluated based on the optical density (OD value) measured using a spectrophotometry: SpectroEye (light source: D65/10) manufactured by X-Rite. The lower the OD value is, the higher the degree of color discharge is. The OD value of the T-shirt before discharge printing was 1.7.

Table 1 summarizes the composition and the evaluation result of each of the reducing agents and the OD value of each of the reducing agents immediately after the preparation in the case where the amounts of thiourea dioxide to be added were 5 wt %, 3.75 wt %, and 2.5 wt % relative to each of the total amounts of the respective reducing agents.

TABLE 1

| | | Ex. | | | | | | | | Comp. Ex. |
|---|---|---|---|---|---|---|---|---|---|---|
| | | 1-1 | 1-2 | 1-2 | 1-4 | 1-5 | 1-6 | 1-7 | 1-8 | 1-9 |
| Reducing agent composition | Thiourea dioxide (TD) | 2.5 to 5 | 2.5 to 5 | 2.5 to 5 | 2.5 to 5 | 2.5 to 5 | 2.5 to 5 | 2.5 to 5 | 2.5 to 5 | 2.5 to 5 |
| | Na formate | 5 | — | — | — | — | — | — | — | — |
| | Na acetate | — | 5 | — | — | — | — | — | — | — |
| | Na glycolate | — | — | 5 | — | — | — | — | — | — |
| | Na thioglycolate | — | — | — | 5 | — | — | — | — | — |
| | Na malonate | — | — | — | — | 5 | — | — | — | — |
| | Na laurate | — | — | — | — | — | 5 | — | — | — |
| | Na pivalate | — | — | — | — | — | — | 5 | — | — |
| | Na trifluoroacetate | — | — | — | — | — | — | — | 5 | — |
| | 2-amino-2-methyl-1-propanol (AMP) | 10 | 10 | 10 | 10 | 10 | 10 | 10 | 10 | 10 |

TABLE 1-continued

|  |  | Ex. | | | | | | | | Comp. Ex. |
| --- | --- | --- | --- | --- | --- | --- | --- | --- | --- | --- |
|  |  | 1-1 | 1-2 | 1-3 | 1-4 | 1-5 | 1-6 | 1-7 | 1-8 | 1-9 |
|  | N-methyl acetoacetic acid amide (NMAA) | 10 | 10 | 10 | 10 | 10 | 10 | 10 | 10 | 10 |
|  | Water | Balance | Balance | Balance | Balance | Balance | Balance | Balance | Balance | Balance |
| OD value | Immediately after preparation (TD: 5 wt %) | 0.295 | 0.31 | 0.417 | 0.433 | 0.381 | 0.325 | 0.389 | 0.383 | 0.435 |
|  | Immediately after preparation (TD: 3.75 wt %) | 0.319 | 0.456 | 0.453 | 0.423 | 0.438 | 0.364 | 0.435 | 0.426 | 0.473 |
|  | Immediately after preparation (TD: 2.5 wt %) | 0.312 | 0.655 | 0.447 | 0.484 | 0.57 | 0.476 | 0.514 | 0.54 | 0.816 |

The unit of reducing agent composition: wt %

Long-Term Stability Evaluation and Indicators of Elapsed Days

Since thiourea dioxide is easily hydrolyzed as mentioned above, the amount of the thiourea dioxide by weight relative to the total amount of the reducing agent is reduced over time after the preparation. Hereinafter, the amount of the thiourea dioxide by weight relative to the total amount of the reducing agent is referred to as TD wt %. Generally, in the case where the TD wt % immediately after the preparation is 5 wt %, the TD wt % is reduced to 3.75 wt % after about three months from immediately after the preparation and is reduced to 2.5 wt % after about six months from immediately after the preparation. Therefore, the reducing agent prepared to have TD wt % of 3.75 wt % was used as an indicator of an OD value of the reducing agent prepared to have a TD wt % of 5 wt %, measured after about three months. The reducing agent prepared to have a TD wt % of 2.5 wt % was used as an indicator of an OD value of the reducing agent prepared to have a TD wt % of 5 wt %, measured after about six months. It generally takes about one month from the preparation of a reducing agent in a manufacturing factory to arrival to the hands of consumers.

TD: 5.0 wt %→TD: 3.75 wt %, after about three months from the preparation

TD: 5.0 wt %→TD: 2.5 wt %, after about six months from the preparation

As summarized in Table 1, in the case where the TD wt % was 5 wt %, Examples 1-1 to 1-8 containing carboxylate exerted a good reducing effect and a prominent reducing ability enhancing effect compared with Comparative Example 1-9 containing no carboxylate. Specifically in each of the cases of containing, as the carboxylate, Na formate (Example 1-1), containing Na acetate (Example 1-2), containing Na malonate (Example 1-5), containing Na laurate (Example 1-6), containing Na pivalate (Example 1-7), and containing Na trifluoroacetate (Example 1-8), the OD value was reduced from 1.7 to 0.4 or less, and a color was discharged significantly.

In the case where the TD wt % was 3.75 wt %, the results demonstrated that Examples 1-1 to 1-8 containing carboxylate exerted a good reducing effect compared with Comparative Example 1-9 containing no carboxylate. As mentioned above, the OD value in the case where the TD wt % was 3.75 wt % corresponds to the OD value of the reducing agent prepared to have TD wt % of 5 wt %, after about 3 months from immediately after the preparation. These results suggest that a low OD value can be maintained even after about three months from immediately after the preparation in the case of containing the specific carboxylate.

In the case where the TD wt % was 2.5 wt %, the results demonstrated that Examples 1-1 to 1-8 containing carboxylate exerted a good reducing effect compared with Comparative Example 1-9 containing no carboxylate. As mentioned above, the OD value in the case where the TD wt % was 2.5 wt % corresponds to the OD value of the reducing agent prepared to have TD wt % of 5 wt %, after about six months from immediately after the preparation. These results suggest that a low OD value can be maintained even after about six months from immediately after the preparation in the case of containing the specific carboxylate.

As described above, the results demonstrated that the reducing ability of each of the reducing agents could be stabilized for at least about six months which is a long period of time by the specific carboxylate.

Examples 2-1 to 2-8

Water, thiourea dioxide, specific carboxylate, 2-amino-2-methyl-1-propanol (AMP) that is a pH adjusting agent in each reducing agent composition summarized in Table 2 were mixed. Subsequently, in Example 2-1, methyl acetoacetate (MAA) and urea were added to the resultant mixture. In each of Examples 2-2 and 2-5, N-methyl acetoacetic acid amide (NMAA) was added to the resultant mixture. In each of Examples 2-4 and 2-8, N-methyl acetoacetic acid amide and urea were added to the resultant mixture. In Example 2-6, acetone was added to the resultant mixture. In Example 2-7, urea was added to the resultant mixture. Thus, the reducing agents of Examples 2-1 to 2-8 were obtained.

The storage stability of each of the reducing agents of Examples 2-1 to 2-8 was evaluated in the same manner as in the evaluation method of Examples 1-1 to 1-8 and Comparative Example 1-9 except that the reducing agents of Examples 2-1 to 2-8 immediately after the preparation, after 0.5 months, 1.0 months, 2.0 months, 3.0 months, 4.0 months, and 5.0 months from the preparation were used.

Table 2 summarizes the composition and the evaluation result of each of the reducing agents of Examples 2-1 to 2-8.

TABLE 2

|  |  | \multicolumn{8}{c}{Examples} |
| --- | --- | --- | --- | --- | --- | --- | --- | --- | --- |
|  |  | 2-1 | 2-2 | 2-3 | 2-4 | 2-5 | 2-6 | 2-7 | 2-8 |
| Reducing agent composition | Thiourea dioxide (TD) | 5 | 5 | 7.5 | 7.5 | 7.5 | 7.5 | 7.5 | 7.5 |
|  | Disodium malonate | 5 | 5 | 5 | 5 | — | 5 | 5 | 5 |
|  | Sodium formate | — | — | — | — | 5 | — | — | — |
|  | 2-amino-2-methyl-1-propanol (AMP) | 10 | 10 | 10 | 10 | 10 | 10 | 10 | 10 |
|  | Methyl acetoacetate (MAA) | 5 | — | — | — | — | — | — | — |
|  | N-methyl acetoacetic acid amide (NMAA) | — | 10 | — | 10 | 10 | — | — | 5 |
|  | Acetone (AC) | — | — | — | — | — | 10 | — | — |
|  | Urea (UR) | 5 | — | — | 5 | — | — | 10 | 5 |
|  | Water | Balance | Balance | Balance | Balance | Balance | Balance | Balance | Balance |
| OD value | Immediately after preparation | 0.329 | 0.355 | 0.295 | 0.302 | 0.345 | 0.319 | 0.234 | 0.279 |
|  | After 0.5 months | 0.297 | 0.405 | 0.378 | 0.341 | 0.377 | 0.351 | 0.307 | 0.339 |
|  | After 1.0 months | 0.291 | 0.337 | 0.381 | 0.359 | 0.334 | 0.402 | 0.328 | 0.328 |
|  | After 2.0 months | 0.305 | 0.437 | 0.426 | 0.369 | 0.483 | 0.408 | 0.374 | 0.316 |
|  | After 3.0 months | 0.314 | 0.444 | 0.48 | 0.351 | 0.347 | 0.361 | 0.423 | 0.306 |
|  | After 4.0 months | 0.35 | 0.401 | 0.582 | 0.356 | 0.346 | 0.349 | 0.367 | 0.284 |
|  | After 5.0 months | 0.393 | 0.437 | 0.557 | 0.298 | 0.28 | — | — | — |

The unit of reducing agent composition: wt %

As summarized in Table 2, the results of Examples 2-1 to 2-2 and 2-4 to 2-8 containing ketone showed low OD values after about 3 months compared with Example 2-3 containing no ketone besides disodium malonate or sodium formate used as the specific carboxylate. Moreover, after about four months, Example 2-3 showed an OD value of 0.5 or more, whereas each of the other examples containing ketone besides disodium malonate or sodium formate or urea showed an OD value of about 0.4 or less, and the difference was significant. In the case where disodium malonate was used as the specific carboxylate (Examples 2-1 to 2-4 and 2-6 to 2-8), each of Examples 2-1, 2-4, and 2-8 using urea together with ketone in combination showed a really low OD value showed that a color of each T-shirt was discharged significantly.

Example 3-1

Water, thiourea dioxide, sodium formate, and 2-amino-2-methyl-1-propanol (AMP) that is a pH adjusting agent in each reducing agent composition summarized in Table 3 were mixed. Subsequently, ketone (N-methyl acetoacetic acid amide (NMAA)) was further added to the resultant mixture. Thus, the reducing agent of Example 3-1 was obtained. As summarized in Table 3, three kinds of reducing agents with the three gradual amounts of thiourea dioxide to be added of 5 wt %, 3.75 wt %, and 2.5 wt % relative to the total amounts of the respective reducing agents were prepared. The same amounts of sodium formate, the pH adjusting agent to be added, and the ketone to be added relative to each of the total amounts of the respective three kinds of reducing agents were used Example 3-2

The reducing agent of Example 3-2 was obtained in the same manner as in Example 3-1 except that the amount of sodium formate to be added was 5 wt % as summarized in Table 3.

Example 3-3

The reducing agent of Example 3-3 was obtained in the same manner as in Example 3-1 except that the amount of sodium formate to be added was 2.5 wt % as summarized in Table 3.

Example 3-4

The reducing agent of Example 3-4 was obtained in the same manner as in Example 3-1 except that the amount of sodium formate to be added was 1.0 wt % as summarized in Table 3.

Example 3-5

The reducing agent of Example 3-5 was obtained in the same manner as in Example 3-2 except that potassium formate was used as a substitute for sodium formate as summarized in Table 3.

The storage stability of each of the reducing agents of Examples 3-1 to 3-5 was evaluated in the same manner as in the evaluation method of Examples 1-1 to 1-8 and Comparative Example 1-9.

Table 3 summarizes the composition and the evaluation result of each of the reducing agents of Examples 3-1 to 3-5. Table 3 also summarizes OD values of each of the reducing agents of Examples 3-1 to 3-5 immediately after the preparation in the cases where the amounts of thiourea dioxide to be added were 5 wt %, 3.75 wt %, and 2.5 wt % relative to the total amounts of the reducing agents.

TABLE 3

|  |  | Examples | | | | |
| --- | --- | --- | --- | --- | --- | --- |
|  |  | 3-1 | 3-2 | 3-3 | 3-4 | 3-5 |
| Reducing agent composition | Thiourea dioxide (TD) | 2.5 to 5 | 2.5 to 5 | 2.5 to 5 | 2.5 to 5 | 2.5 to 5 |
|  | Na formate | 10 | 5 | 2.5 | 1 |  |
|  | K formate |  |  |  |  | 5 |
|  | 2-amino-2-methyl-1-propanol (AMP) | 10 | 10 | 10 | 10 | 10 |
|  | N-methyl acetoacetic acid amide (NMAA) | 5 | 5 | 5 | 5 | 5 |
|  | Water | Balance | Balance | Balance | Balance | Balance |
| OD value | Immediately after preparation (TD: 5 wt %) | 0.281 | 0.278 | 0.317 | 0.316 | 0.313 |
|  | Immediately after preparation (TD: 3.75 wt %) | 0.271 | 0.293 | 0.303 | 0.316 | 0.31 |
|  | Immediately after preparation (TD: 2.5 wt %) | 0.328 | 0.335 | 0.376 | 0.397 | 0.336 |

The unit of reducing agent composition: wt %

As summarized in Table 3, the results of Examples 3-2 to 3-5 showed OD values of about 0.3 which was really low in the case where the TD wt % of potassium formate was 5 wt % as in the sodium formate. As described above, the results demonstrated that the reducing agent enhancing effect was exerted in the case of using potassium formate as in the case of using sodium formate.

In both of the cases where the TD wt % was 3.75 wt % and 2.5 wt %, Example 3-5 showed an OD value of 0.35 or less, and the result demonstrated that the long-term stability effect was exerted in the case of using potassium formate as in the case of using sodium formate.

In the case where the TD wt % was 5 wt %, Examples 3-1 to 3-4 in which the concentrations of sodium formate were only changed showed an OD value of about 0.3 which was really low even when the amount of sodium formate to be added was 1 wt %. Please note that when the amount of sodium formate to be added is increased, a result may show a lower OD value. When the amount of sodium formate to be added was 5 wt % or more, a result demonstrated the improvement in reducing agent enhancing effect. In each of the cases where the TD wt % was 3.75 wt % and 2.5 wt %, an OD value was 0.4 or less which was really low, and the result demonstrated that a long-term stability effect is exerted.

Examples 4-1 to 4-35

Water, thiourea dioxide (TD), specific carboxylate (Na formate), a PH adjusting agent (AMP), and NMAA in each reducing agent composition (Table 4) were mixed. Thus, the reducing agents of Examples 4-1 to 4-7 were obtained. Moreover, the reducing agents of Examples 4-8 to 4-14, 4-15 to 4-21, 4-22 to 4-28, 4-29 to 4-35 were obtained in the same manner as in Examples 4-1 to 4-7 except that the amounts of Na formate were changed. The storage stability of each of the reducing agents of Examples 4-1 to 4-35 was evaluated in the same evaluation method as in Examples 1-1 to 1-8 except that the storage stability of not only the reducing agents of Examples 4-1 to 4-35 immediately after the preparation but also the reducing agents of Examples 4-1 to 4-35 after 0.5 months from the preparation were evaluated. The evaluation results are summarized in Tables 4 to 8. Please note that as to Examples 4-6 to 4-7, 4-13 to 4-14, 4-20 to 4-21, 4-27 to 4-28, and 4-34 to 4-35, the evaluation of the reducing agent after 0.5 months was only performed.

TABLE 4

|  |  | Examples | | | | | | |
| --- | --- | --- | --- | --- | --- | --- | --- | --- |
|  |  | 4-1 | 4-2 | 4-3 | 4-4 | 4-5 | 4-6 | 4-7 |
| Reducing agent composition | TD | 2 | 3 | 4 | 5 | 7.5 | 10 | 12.5 |
|  | Na formate | 1 | 1 | 1 | 1 | 1 | 1 | 1 |
|  | AMP | 10 | 10 | 10 | 10 | 10 | 10 | 10 |
|  | NMAA | 5 | 5 | 5 | 5 | 5 | 5 | 5 |
|  | Water | Balance | Balance | Balance | Balance | Balance | Balance | Balance |
| OD value | Immediately after preparation | 0.523 | 0.431 | 0.416 | 0.344 | 0.338 | — | — |
|  | After 0.5 months | 0.606 | 0.553 | 0.419 | 0.387 | 0.392 | 0.559 | 0.575 |

The unit of reducing agent composition: wt %

TABLE 5

|  |  | Examples | | | | | | |
| --- | --- | --- | --- | --- | --- | --- | --- | --- |
|  |  | 4-8 | 4-9 | 4-10 | 4-11 | 4-12 | 4-13 | 4-14 |
| Reducing agent composition | TD | 2 | 3 | 4 | 5 | 7.5 | 10 | 12.5 |
|  | Na formate | 2.5 | 2.5 | 2.5 | 2.5 | 2.5 | 2.5 | 2.5 |
|  | AMP | 10 | 10 | 10 | 10 | 10 | 10 | 10 |

TABLE 5-continued

|  |  | Examples | | | | | | |
| --- | --- | --- | --- | --- | --- | --- | --- | --- |
|  |  | 4-8 | 4-9 | 4-10 | 4-11 | 4-12 | 4-13 | 4-14 |
|  | NMAA | 5 | 5 | 5 | 5 | 5 | 5 | 5 |
|  | Water | Balance | Balance | Balance | Balance | Balance | Balance | Balance |
| OD value | Immediately after preparation | 0.473 | 0.454 | 0.369 | 0.35 | 0.338 | — | — |
|  | After 0.5 months | 0.569 | 0.511 | 0.408 | 0.362 | 0.361 | 0.492 | 0.488 |

The unit of reducing agent composition: wt %

TABLE 6

|  |  | Examples | | | | | | |
| --- | --- | --- | --- | --- | --- | --- | --- | --- |
|  |  | 4-15 | 4-16 | 4-17 | 4-18 | 4-19 | 4-20 | 4-21 |
| Reducing agent composition | TD | 2 | 3 | 4 | 5 | 7.5 | 10 | 12.5 |
|  | Na formate | 5 | 5 | 5 | 5 | 5 | 5 | 5 |
|  | AMP | 10 | 10 | 10 | 10 | 10 | 10 | 10 |
|  | NMAA | 5 | 5 | 5 | 5 | 5 | 5 | 5 |
|  | Water | Balance | Balance | Balance | Balance | Balance | Balance | Balance |
| OD value | Immediately after preparation | 0.447 | 0.405 | 0.411 | 0.352 | 0.313 | — | — |
|  | After 0.5 months | 0.555 | 0.416 | 0.395 | 0.334 | 0.377 | 0.395 | 0.417 |

The unit of reducing agent composition: wt %

TABLE 7

|  |  | Examples | | | | | | |
| --- | --- | --- | --- | --- | --- | --- | --- | --- |
|  |  | 4-22 | 4-23 | 4-24 | 4-25 | 4-26 | 4-27 | 4-28 |
| Reducing agent composition | TD | 2 | 3 | 4 | 5 | 7.5 | 10 | 12.5 |
|  | Na formate | 7.5 | 7.5 | 7.5 | 7.5 | 7.5 | 7.5 | 7.5 |
|  | AMP | 10 | 10 | 10 | 10 | 10 | 10 | 10 |
|  | NMAA | 5 | 5 | 5 | 5 | 5 | 5 | 5 |
|  | Water | Balance | Balance | Balance | Balance | Balance | Balance | Balance |
| OD value | Immediately after preparation | 0.437 | 0.382 | 0.373 | 0.337 | 0.362 | — | — |
|  | After 0.5 months | 0.518 | 0.401 | 0.417 | 0.367 | 0.359 | 0.392 | 0.437 |

The unit of reducing agent composition: wt %

TABLE 8

|  |  | Examples | | | | | | |
| --- | --- | --- | --- | --- | --- | --- | --- | --- |
|  |  | 4-29 | 4-30 | 4-31 | 4-32 | 4-33 | 4-34 | 4-35 |
| Reducing agent composition | TD | 2 | 3 | 4 | 5 | 7.5 | 10 | 12.5 |
|  | Na formate | 10 | 10 | 10 | 10 | 10 | 10 | 10 |
|  | AMP | 10 | 10 | 10 | 10 | 10 | 10 | 10 |
|  | NMAA | 5 | 5 | 5 | 5 | 5 | 5 | 5 |
|  | Water | Balance | Balance | Balance | Balance | Balance | Balance | Balance |
| OD value | Immediately after preparation | 0.47 | 0.367 | 0.376 | 0.371 | 0.355 | — | — |
|  | After 0.5 months | 0.561 | 0.475 | 0.479 | 0.398 | 0.406 | 0.374 | 0.375 |

The unit of reducing agent composition: wt %

As summarized in Tables 4 to 8, in both of the cases of the reducing agents immediately after the preparation and the reducing agents after 0.5 months (only the case of the reducing agents after 0.5 months in the case where only the evaluation of the reducing agents after 0.5 months were evaluated), Examples 4-1 to 4-35 showed low OD values. When the examples in which only the amounts of TD to be added were different were compared in each of Tables 4 to 8, the results showed lower measured OD values of the reducing agents immediately after the preparation and the reducing agents after 0.5 months in the cases where the amounts of TD to be added were 3 wt % to 12.5 wt %. The results of Examples 4-1 to 4-7 and 4-8 to 4-14 having the amounts of Na formate to be added of 1 wt % to 2.5 wt % showed low OD values of the reducing agents after 0.5 months in the cases where the amounts of TD to be added were 5 wt % to 7.5 wt %. Examples 4-15 to 4-21 having the amounts of Na formate to be added of 5 wt % showed lower OD values of the reducing agents after 0.5 months in the cases where the amounts of TD to be added were 4 wt % to 10 wt %. The results of Examples 4-22 to 4-28 having the amounts of Na formate to be added of 7.5 wt % showed further lower OD values of the reducing agents after 0.5 months in the cases where the amounts of TD to be added were 5 wt % to 10 wt %. The results of Examples 4-29 to 4-35 having the amounts of Na formate to be added of 10 wt % showed yet further lower OD values of the reducing agent after 0.5 months in the cases where the amounts of TD to be added were 5 wt % to 12.5 wt %. That is, regardless of the amount of Na formate to be added, in the cases where the amounts of TD to be added were 5 wt % to 7.5 wt %, the results showed a low OD value which was further favorable. In the cases where the amounts of TD to be added were 10 wt % to 12.5 wt %, although OD values were low, gas was generated when the reducing agents were stored. This generation of gas does not directly influence on the reducing ability. For example, from the viewpoint of preventing the generation of gas at the time when the reducing agent is stored in the cases where the reducing agent is stored in an airtight container for a long period of time, and the reducing agent is applied to fabric using a head of an ink-jet recording apparatus, the amount of TD to be added is, for example, 7.5 wt % or less.

As summarized in Tables 4 to 8, the results of Examples 4-1 to 4-35 showed low OD values of the reducing agents after 0.5 months. When the examples in which only the amounts of specific carboxylate (Na formate) to be added were different in the case where the amounts of TD to be added were 2 wt %, 3, wt %, 4 wt %, 5 wt %, 7.5 wt %, 10 wt %, and 12.5 wt % were compared in each of Tables 4 to 8, the results of Examples 4-2, 4-9, 4-16, 4-23, and 4-30 having the amounts of TD to be added of 3 wt % showed lower measured OD values of the reducing agents after 0.5 months in the cases where the amount of Na formate to be added were 5 wt % to 10 wt %. The results of Examples 4-3, 4-10, 4-17, 4-24, and 4-31 having the amounts of TD to be added of 4 wt % showed low OD values regardless of the amount of Na formate to be added and a lower OD value in the case where the amounts of Na formate to be added were 1 wt % to 7.5 wt %. The results of Examples 4-4 to 4-5, 4-11 to 4-12, 4-18 to 4-19, 4-25 to 4-26, and 4-32 to 4-33 having the amounts of TD to be added of 5 wt % to 7.5 wt % showed low OD values which were favorable regardless of the amount of Na formate to be added and showed lower OD values specifically in the case where the amounts of Na formate to be added were 2.5 wt % to 7.5 wt %. The results of Examples 4-6 to 4-7, 4-13 to 4-14, 4-20 to 4-21, 4-27 to 4-28, and 4-34 to 4-35 having the amounts of TD to be added of 10 wt % to 12.5 wt % showed further lower OD values in the cases where the amounts of Na formate to be added were 5 wt % to 10 wt %. That is, regardless of the amount of TD to be added, in the cases where the amounts of Na formate to be added were 5 wt % to 7.5 wt %, the results showed low OD values which were further favorable.

The lower the OD value is, the more the color of the T-shirt as an example of fabric is discharged. As to the OD values in Tables 4 to 8, specifically when the OD value was less than 0.4, the difference between the state of the T-shirt having an OD value of 0.4 or less and the state of the T-shirt after color discharge is difficult to be distinguished by visual check. Therefore, in the case where the reducing agents of the examples are used as discharge printing agents for fabric, the OD value of less than 0.4 is a further favorable state, and it may be determined that a pigment in fabric is sufficiently discharged. Specifically in the case where the reducing agent of the present invention is used as a discharge printing agent for fabric, the OD value is less than 0.4 which is a favorable result for a discharge printing agent for fabric in the cases where the amounts of TD to be added are 5 wt % to 7 wt % and the amounts of Na formate to be added are 1 wt % to 7.5 wt %.

It will be obvious to those having skill in the art that many changes may be made in the above-described details of the particular aspects described herein without departing from the spirit or scope of the invention as defined in the appended claims.

What is claimed is:

1. A reducing agent comprising:
thiourea dioxide; and
carboxylate, wherein
the carboxylate comprises at least one selected from the group consisting of aliphatic monocarboxylate, an aliphatic monocarboxylic acid derivative salt, and malonate; and
wherein a pH of the reducing agent is in a range from pH8 to pH10.

2. The reducing agent according to claim 1, wherein
the aliphatic monocarboxylate is at least one selected from the group consisting of formate, laurate, and pivalate, and
the aliphatic monocarboxylic acid derivative salt is trifluoroacetate.

3. The reducing agent according to claim 1, wherein
the carboxylate comprises formate or laurate.

4. The reducing agent according to claim 1 further comprising a pH adjusting agent.

5. The reducing agent according to claim 1 further comprising urea or ketone.

6. The reducing agent according to claim 5 comprising ketone, wherein
the ketone is β-diketone or a compound represented by the following general formula (1):

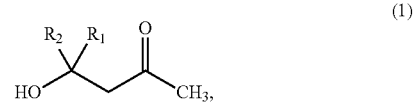

(1)

where in the general formula (1),
$R_1$ and $R_2$ each represents a straight-chain or a branched alkyl group with a carbon number of 1 to 20 or hydrogen and are identical to or different from each other.

7. The reducing agent according to claim 5 comprising ketone, wherein the ketone is at least one β-diketone selected from the group consisting of acetylacetone, 3-acetyl-γ-butyrolactone, dehydroacetic acid, methyl acetoacetate, and N-methyl acetoacetic acid amide.

8. The reducing agent according to claim 7, wherein the β-diketone is N-methyl acetoacetic acid amide.

9. The reducing agent according to claim 1, wherein the amount of the thiourea dioxide to be added is 5 wt % to 7.5 wt % relative to the total amount of the reducing agent.

10. The reducing agent according to claim 9, wherein the carboxylate is formate, and
the amount of the formate to be added is 1 wt % to 7.5 wt % relative to the total amount of the reducing agent.

11. The reducing agent according to claim 1, wherein the amount of the carboxylate to be added is 1 wt % to 7.5 wt % relative to the total amount of the reducing agent.

12. An ink-jet recording apparatus comprising a liquid ejection unit that ejects a liquid and further comprising a unit that applies a reducing agent, wherein
the reducing agent is the reducing agent according to claim 1.

13. A method for discharge printing of fabric, comprising:
a reducing agent applying step of applying a reducing agent to fabric; and
a heating step of heating a reducing agent-applied area, wherein
as the reducing agent, the reducing agent according to claim 1 is used.

14. A method for forming an image on fabric, comprising:
a discharge printing step of performing discharge printing of fabric; and
an image printing step of printing an image on a discharge printing-performed area using an ink, wherein
the discharge printing step is performed by the method according to claim 13.

15. A method for stabilizing a reducing agent that comprises thiourea dioxide, comprising: adding carboxylate, wherein the carboxylate is at least one selected from the group consisting of aliphatic monocarboxylate, aliphatic monocarboxylic acid derivative salt, and malonate; and wherein a pH of the reducing agent is in a range from pH8 to pH 10.

16. A method for enhancing a reducing agent that comprises thiourea dioxide, comprising: adding carboxylate; wherein the carboxylate is at least one selected from the group consisting of aliphatic monocarboxylate, aliphatic monocarboxylic acid derivative salt, and malonate; and wherein a pH of the reducing agent is in a range from pH8 to pH10.

* * * * *